United States Patent [19]

Jackson

[11] Patent Number: 5,831,075

[45] Date of Patent: Nov. 3, 1998

[54] AMINO ACID ESTER OF NUCLEOSIDE ANALOGUES

[75] Inventor: William Paul Jackson, Kent, England

[73] Assignee: Rolabo SL, Zaragoza, Spain

[21] Appl. No.: 564,080

[22] PCT Filed: Jun. 9, 1994

[86] PCT No.: PCT/GB94/01245

§ 371 Date: Jun. 3, 1996

§ 102(e) Date: Jun. 3, 1996

[87] PCT Pub. No.: WO94/29311

PCT Pub. Date: Dec. 22, 1994

[30] Foreign Application Priority Data

Jun. 10, 1993 [GB] United Kingdom .................... 9311952
Oct. 7, 1993 [GB] United Kingdom .................... 9320645

[51] Int. Cl.$^6$ ....................................................... C07H 1/00
[52] U.S. Cl. .................. 536/27.14; 536/27.8; 536/27.81; 536/28.2; 536/28.5; 536/28.53; 536/28.54; 536/124; 536/125
[58] Field of Search ................................. 514/45, 46, 47, 514/48, 49, 50, 51, 256, 261, 269; 536/27.14, 27.8, 27.81, 28.2, 28.5, 28.53, 28.54, 124, 125; 544/137, 138

[56] References Cited

U.S. PATENT DOCUMENTS 5,318,974  6/1994  Beauchamp .

FOREIGN PATENT DOCUMENTS 0 099 493 B1  8/1989  European Pat. Off. .
0 308 065 B1  1/1995  European Pat. Off. .
0 596 542 B1  5/1996  European Pat. Off. .

Primary Examiner—James O. Wilson
Attorney, Agent, or Firm—Testa, Hurwitz & Thibeault, LLP

[57] ABSTRACT

A process for the preparation of an amino acid ester of a nucleoside analogue comprises reacting a nucleoside analogue having an esterifiable hydroxy group with a 2-oxa-4-aza-cycloalkane-1,3-dione. Such amino acid esters of nucleoside analogues are able to interfere with viral nucleic acid metabolism and are therefore useful for their anti-viral activity.

10 Claims, No Drawings

AMINO ACID ESTER OF NUCLEOSIDE ANALOGUES

The present invention relates to an improved new process for the preparation of amino acid esters of nucleoside analogues.

Nucleoside analogues constitute an important class of drugs useful predominantly for their anti-viral activity. Their major therapeutic effect thus stems from their ability to interfere with viral nucleic acid metabolism, notably DNA or RNA replication. A great number of nucleoside analogues have been described and many have found clinical application in treating a variety of viral infections. Thus acyclovir (9-(2-hydroxyethoxymethyl)guanine) and BW 882C are particularly useful against Herpes virus (see e.g. Schaeffer et al., Nature 272 583–585, 1978) whereas AZT (azidothymidine, zidovudine, retrovir) and more recently ddI (dideoxyinosine) have been proposed, and indeed are used, for the treatment of AIDS and HIV infection.

Efforts continue to develop new and improved nucleoside analogues and in recent years such efforts have included derivatisation of existing nucleoside analogues to improve their properties, for example in terms of bioactivity, bioavailability, or to facilitate their formulation, eg. by enhancing water solubility.

Thus for example amino acid esters of nucleoside analogues have been synthesised. EP-A-308065 and EP-A-99493 of Wellcome describe, respectively, the valine and isoleucine, and glycine and alanine, esters of acyclovir.

Such amino acid esters are typically synthesized, as described for example in EP-A-303065, through a direct esterification reaction between the free hydroxy group of the nucleoside analogue and the carboxy group of the amino acid. Certain alternative reaction routes however have been described in EP-A-308065.

The prior art processes described and used are however generally multi-step processes involving for example protection and deprotection stages, and requiring costly reagents. Thus activating and/or coupling reagents (such as DCC and DMAP) are frequently required to achieve the desired reaction, adding both to costs and reaction complexity. A need therefore exists for improved processes for the preparation of amino acid nucleoside analogue esters, which are more economical, quicker and above all simpler to perform. The present invention provides just such a process.

In one aspect the present invention thus provides a process for the preparation of an amino acid ester (i.e. a mono, di, tri or polyester) of a nucleoside analogue, said process comprising reacting a nucleoside analogue having an esterifiable hydroxy group in its linear or cyclic ether moiety, with an optionally ring-carbon substituted 2-oxa-4-aza-cycloalkane-1,3-dione.

Naturally occurring nucleosides have two components, a nitrogen-containing purine or pyrimidine ring structure, linked to a sugar ring of ribose or deoxyribose. Such nucleosides form the building blocks of DNA and RNA and are thus recognised by and interact with DNA/RNA synthesising enzymes, including the enzymes of infecting viruses. Either or both of the purine/pyrimidine or sugar components of naturally occurring nucleosides may be altered to create an analogue which is still recognised by the viral machinery but which cannot function as a normal substrate. The nucleoside analogue can thus inhibit enzyme function and/or impair the resulting nucleic acid structure (e.g. by chain termination or base pair mismatching). The term "nucleoside analogue" as used herein covers such analogues.

In many nucleoside analogues, modification of the "sugar" moiety results in an alteration of the chemical nature of the group such that it can no longer correctly be referred to as a sugar; as used herein "ether moiety" describes the group in the analogue resulting from the sugar group modification, and it may be cyclic (as in AZT, ddI and related analogues), or linear, (as in acyclovir or 9-(1,3-dihydroxy-2-propoxymethyl)guanine, DHPG). Nucleoside analogues are described extensively in the literature, and many are listed for example in Nasr et al., Antiviral Research 14, 125–148 (1990) or McGowan et al., Antiviral Chemotherapy, Volume 2, 333–345, Ed. Mills and Corely, 1989.

Preferred for use according to the invention, are nucleoside analogues having cyclic ether groups based on saturated or unsaturated furanose rings as exemplified for example by AZT, BW 882C CS-87 (Azddu, 3'-azido-2,3'-dideoxyuridine), D4T (2',3'-dideoxydidehydrothymidine), 3'-deoxy-3'-fluorothymidine (3'-FddT, FLT), 2'3'dideoxycytidine (ddC), 2'3'-dideoxyinosine (ddI), carbocyclic (2',3'-didehydro-2',3'-dideoxyguanosine) (carbovir,carbocyclic-D4G) and the many others listed in Nasr et al. (Supra) or acyclic ether groups such as those of acyclovir, pencyclovir (Smith Kline Beecham), DHPG and related analogues (Nasr et al., Supra).

The optionally ring-carbon substituted 2-oxa-4-aza cycloalkane-1,3-dione reagent can be perceived as a cyclic carbonic acid condensation product of an amino acid, the side chain of the amino acid providing the optional ring carbon substitution, and serves to introduce the amino acid component into the final ester product.

This new process of the invention may be performed in a single step without the need for protection and subsequent deprotection of chemically reactive groups and is thus much simpler and quicker to perform than the previously reported procedures. Furthermore the reagents which are used are sufficiently reactive that coupling/activating agents will generally not be required. The process of the invention thus also has the advantage of greater cost effectiveness (fewer and less costly reagents) and is safer to perform.

The 2-oxa-4-aza-cycloalkane-1,3-dione is preferably a 4-substituted oxazolidine-2,5-dione and yields α-amino acid ester products, although other compounds falling within the general 2-oxa-4-aza cycloalkane-1,3-dione definition e.g., oxaazacyclohexanediones, may be used to produce other eg. β-amino acid, ester products.

The 4-substituent of the oxazolidine-2,5-dione represents the side chain of the corresponding amino acid and is therefore selected according to the amino acid it is desired to esterify.

Thus the 2-oxa-4-aza-cycloalkane-1,3-dione may be represented by the formula

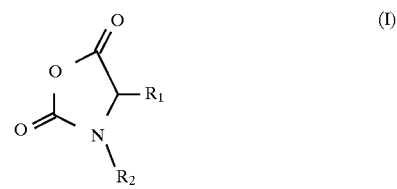

wherein $R_1$ may represent hydrogen, $C_{1-4}$-alkyl (eg. methyl, isopropyl or isobutyl) or alkenyl group or other amino acid side chains, such as those commonly described in the literature, and $R_2$ may represent hydrogen or a group $COOR_3$ where $R_3$ is a benzyl, t-butyl, fluorenylmethyl or an optionally halo (eg. chloro, bromo, fluoro or iodo, especially chloro or bromo) substituted linear or branched $C_{1-8}$-alkyl group. Conveniently the group $R_1$ may be selected from among the side-chains of the twenty well known key α-amino acids found in proteins.

Preferred $R_1$ groups are non-ionizable, and more preferably are also non-polar. Particularly preferred groups $R_1$ include hydrogen, methyl, iso-propyl and isobutyl representing respectively the side chains of the α-amino acids glycine, alanine, valine and isoleucine.

Preferred 2-oxa-4-aza-cycloalkane-1,3-diones are those of formula I wherein $R_2$ denotes a group $COOR_3$ and $R_3$ denotes a benzyl group or a t-butyl group. Particularly preferably said group $COOR_3$ is subsequently deprotected.

Preferably, but not essentially, the optionally ring-carbon substituted 2-oxaazacycloalkanedione reagent is selected so as to introduce an amino acid having the L configuration into the final ester product, although D or DL racemic forms may also be prepared.

In particularly preferred embodiments, the process of the invention is effected using acylovir and an optionally protected oxaazacyclopentanedione selected from oxazolidine-2,5-dione and its 4-methyl-,4-isopropyl-and 4-isobutyl derivatives, yielding respectively the optionally protected glycine, alanine, valine and isoleucine esters of acyclovir. Where the process of the invention leads to protected nucleoside analogue esters, the protecting group is preferably removed by, for example, conventional means. The ester pro-drugs, after such removal of the protecting group, have improved bioavailability over the parent drug (e.g acyclovir) thereby enabling lower dosages and a less frequent dosing regime to be used in treating viral infections responsive to the drug.

Generally, the process is carried out in the presence of a solvent in which the nucleoside analogue is at least partially soluble. Thus in the case of acyclovir, N-methyl-pyrolidinone or dimethylformamide may for example be used.

The process is conveniently carried out at temperatures between the freezing and boiling points of the reaction mixture, but the preferred temperatures are in the range of 10° C.–80° C.

It will be appreciated that the process of the invention may be used to prepare hitherto undescribed amino acid nucleoside analogue esters and such novel esters accordingly form a further aspect of this invention.

The invention will now be described by reference to the following non-limiting Examples in which all parts, ratios and percentages are by weight unless otherwise stated:

EXAMPLE 1

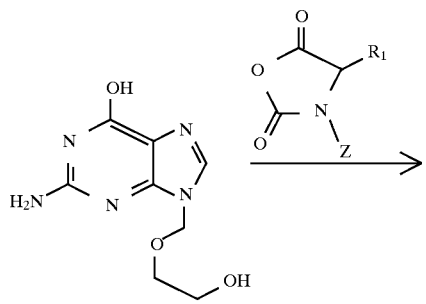

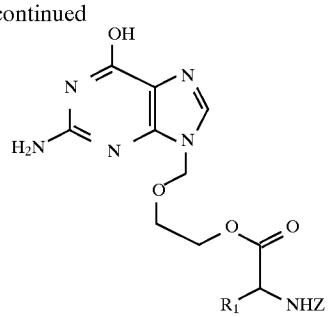

(where Z is $CO_2CH_2C_6H_5$)

Acyclovir (1 g) is dissolved in 12 ml of N-methyl pyrolidinone at 100°–110° C. The solution is cooled to ambient temperature and DMAP (4-dimethyl amino pyridine) (50 mg) and Z-valine NCA (N-carboxyanhydride) (1.45 g, from propeptide) is added. Carbon dioxide is monitored by use of a gas bubbler. When evolution of gas has ceased, the solvent is removed under high vacuum at 60° C. The residue is storer with 20 ml 1M HCl, filtered and the white solid is washed with water. After drying, 2.2 g of solid is obtained (theory 2.25) which is about 95 per cent pure by Hc, with the impurity being Z-valine. The material is sufficiently pure for deprotection, or may be crystallised to purify further.

EXAMPLE 2

Acyclovir (1 g) is suspended in dry DMF (10 ml). DMAP (50 mg) and Z-valine NCA (1.45 g) is added. The mixture is warmed to 55°–60° C. until evolution of carbon dioxide has ceased (0.5 L) and a clear solution is obtained. The solvent is removed and the residue is treated with 20 ml 1M HCl. The solid is filtered and washed with water. After drying, a yield of 1.8 grams is obtained.

EXAMPLE 3

Acyclovir (2.36 g, 10.5 MMole), Z-valine NCA (2.93 g, 10 MMole) and DMAP (50 mg) are mixed in DMF (10 ml). The reaction mixture is gradually heated to 55° C. When all evolution of gas has ceased, the mixture is cooled to ambient temperature, the excess acyclovir filtered, and the solvent removed under vacuum. The mixture is treated as in the previous Examples to obtain 4.3 grams of product.

EXAMPLE 4

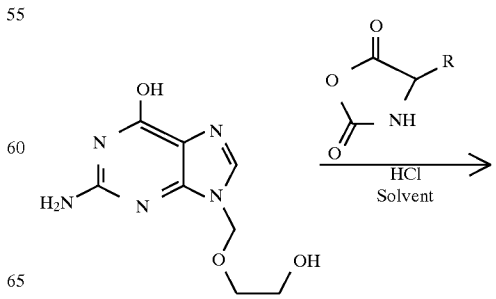

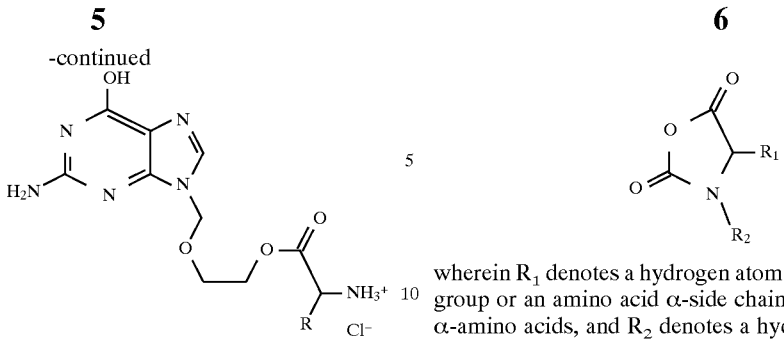

A suspension of acyclovir (2 g) is suspended in dry, dimethylformamide (150 ml) and warmed to 60° C. At this temperature sufficient volume of a saturated solution of hydrogen chloride in dioxan is added such that 10 equivalents of hydrogen chloride are present. To this mixture is rapidly added 1–2 equivalents of the appropriate 4-substituted oxazolidine-2,5-dione. The reaction is stirred for between 2 and 48 hours while cooling to ambient temperature. Excess hydrogen chloride and dioxan are removed under reduced pressure. The dimethylformamide is removed under higher vacuum and elevated temperature (<60° C.) and may be re-used. The residue is taken up in warm aqueous ethanol, filtered to remove unreacted acyclovir (which may be re-used) and the product crystallised by cooling.

I claim:

1. A process for the preparation of an amino acid ester of a nucleoside analogue, said process comprising reacting a nucleoside analogue having an esterifiable hydroxy group in its linear or cyclic ether moiety with a 2-oxa-4-aza-cycloalkane-1,3-dione.

2. A process as claimed in claim 1 wherein said 2-oxa-4-aza-cycloalkane-1,3-dione is substituted at a ring carbon.

3. A process as claimed in claim 1, wherein said 2-oxa-4-aza-cycloalkane-1,3-dione is a compound of formula I:

wherein $R_1$ denotes a hydrogen atom, a $C_{1-4}$-alkyl or alkenyl group or an amino acid α-side chain of the protein-forming α-amino acids, and $R_2$ denotes a hydrogen atom or a group $COOR_3$ where $R_3$ is benzyl, t-butyl, fluorenylmethyl, a linear or branched $C_{1-8}$-alkyl group, or a halo-substituted linear or branched $C_{1-8}$-alkyl group.

4. A process as claimed in claim 3 wherein said 2-oxa-4-aza-cycloalkane-1,3-dione is a compound of formula I, wherein $R_1$ denotes a hydrogen atom or a methyl, isopropyl or isobutyl group.

5. A process as claimed in claim 3 wherein said 2-oxa-4-aza-cycloalkane-1,3-dione is a compound of formula I, wherein $R_2$ denotes a group $COOR_3$ and $R_3$ denotes a benzyl group.

6. A process as claimed in claim 3 wherein said 2-oxa-4-aza-cycloalkane-1,3-dione is a compound of formula I, wherein $R_2$ denotes a group $COOR_3$ and $R_3$ denotes a t-butyl group.

7. A process as claimed in claim 3 comprising the additional step of deprotecting said group $COOR_3$ after said reaction step.

8. A process as claimed in claim 1 wherein said nucleoside analogue is acyclovir.

9. A process as claimed in claim 1 wherein said nucleotide analogue is 9-(1, 3-dihydroxy-2-propoxymethyl)guanine.

10. A process as claimed in claim 1, wherein said nucleoside analogue is reacted with a compound having an asymmetric carbon atom to yield said ester containing the amino acid residue in the L-configuration.

* * * * *